United States Patent [19]
Smith, Sr.

[11] Patent Number: 6,045,519
[45] Date of Patent: Apr. 4, 2000

[54] INFLATABLE SUPPORT DEVICE

[76] Inventor: Joseph D. Smith, Sr., 8269 Bernard Dr. South, Millersville, Md. 21108

[21] Appl. No.: 09/156,094

[22] Filed: Sep. 17, 1998

[51] Int. Cl.[7] .............................. A61G 5/00; A61G 15/00
[52] U.S. Cl. ............................... 602/13; 602/5; 128/845; 128/DIG. 20
[58] Field of Search ................................... 602/5, 19, 13, 602/60–62; 128/DIG. 20, 845, 869, 876, 100.1, 102.1, 118.1; 36/88, 89; 482/55, 124; 441/106, 108–110, 113, 119, 120, 125, 126

[56] References Cited

U.S. PATENT DOCUMENTS

| | | | |
|---|---|---|---|
| 1,468,072 | 9/1923 | Ogle | 128/889 |
| 2,667,917 | 2/1954 | Dustin | 128/845 |
| 3,308,813 | 3/1967 | Loeffel | 128/96.1 |
| 3,521,623 | 7/1970 | Nichols | 602/13 |
| 5,158,767 | 10/1992 | Cohen et al. | 36/88 |
| 5,253,435 | 10/1993 | Auger et al. | 36/88 |
| 5,437,615 | 8/1995 | Pekar et al. | 602/19 |
| 5,547,461 | 8/1996 | Levis | 602/19 |
| 5,762,622 | 6/1998 | Lamont | 602/65 |
| 5,876,364 | 3/1999 | Herbst | 602/27 |

*Primary Examiner*—Richard J. Apley
*Assistant Examiner*—Denise Pothier

[57] ABSTRACT

An inflatable support device for supporting the lower back of a user especially when the user is sitting. The device includes an elongate flexible belt adapted for wrapping around the waist area of a wearer. An inflatable waist bladder is coupled to the belt such that the waist bladder is wrapped around the waist area of the wearer when the belt is wrapped around the waist area of the wearer. An elongate lower support bar downwardly depends from the belt. The lower support bar is designed for positioning adjacent the spine region of the lower back area of the wearer to provide support to the lower back area of the wearer. The lower support bar has opposite top and bottom ends, and a pair of side edges extending between the top and bottom ends of the lower support bar. The top end of the lower support bar is attached to the belt. A flexible flap is extended from the bottom end of the lower support bar. The flexible flap is designed for sitting on by the wearer. The lower support bar has a pair of elongate inflatable back bladders. One of the back bladders is coupled to one of the side edges of the lower support bar. The other back bladder is coupled to the other side edge of the lower support bar.

10 Claims, 3 Drawing Sheets

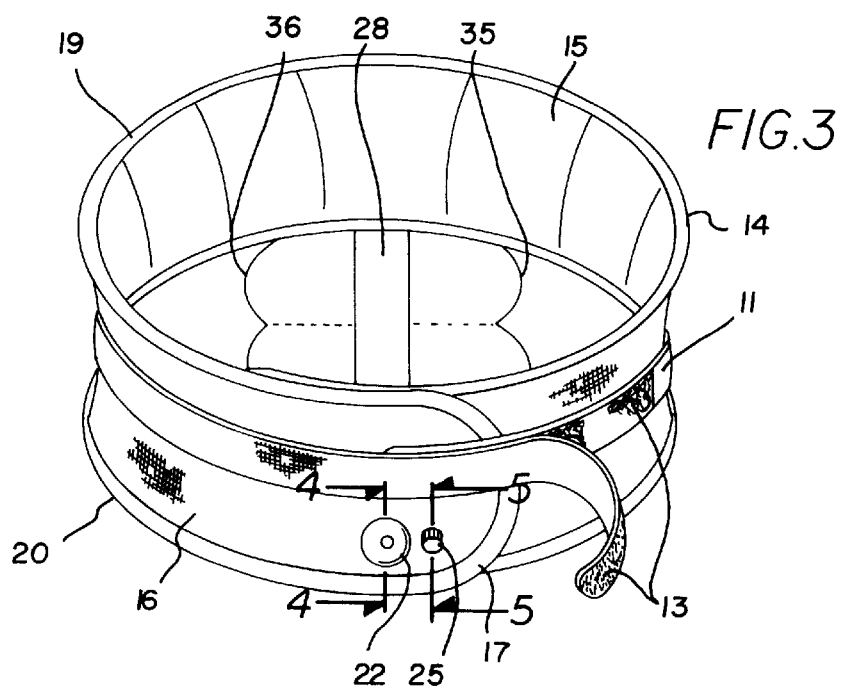
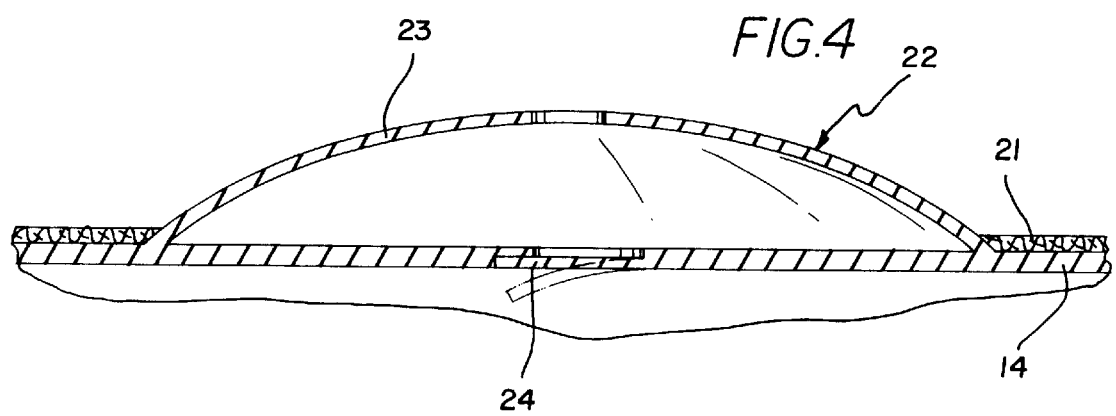

INFLATABLE SUPPORT DEVICE

BACKGROUND OF THE INVENTION

1. Field of the Invention

The present invention relates to support belts and more particularly pertains to a new inflatable support device for supporting the lower back of a user especially when the user is sitting.

2. Description of the Prior Art

The use of support belts is known in the prior art. More specifically, support belts heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,437,615; 5,396,906; 5,195,948; 4,135,503; 3,452,748; and U.S. Pat. No. Des. 302,874.

While these devices fulfill their respective, particular objectives and requirements, the aforementioned patents do not disclose a new inflatable support device. The inventive device includes an elongate flexible belt adapted for wrapping around the waist area of a wearer. An inflatable waist bladder is coupled to the belt such that the waist bladder is wrapped around the waist area of the wearer when the belt is wrapped around the waist area of the wearer. An elongate lower support bar downwardly depends from the belt. The lower support bar is designed for positioning adjacent the spine region of the lower back area of the wearer to provide support to the lower back area of the wearer. The lower support bar has opposite top and bottom ends, and a pair of side edges extending between the top and bottom ends of the lower support bar. The top end of the lower support bar is attached to the belt. A flexible flap is extended from the bottom end of the lower support bar. The flexible flap is designed for sitting on by the wearer. The lower support bar has a pair of elongate inflatable back bladders. One of the back bladders is coupled to one of the side edges of the lower support bar. The other back bladder is coupled to the other side edge of the lower support bar.

In these respects, the inflatable support device according to the present invention substantially departs from the conventional concepts and designs of the prior art, and in so doing provides an apparatus primarily developed for the purpose of supporting the lower back of a user especially when the user is sitting.

SUMMARY OF THE INVENTION

In view of the foregoing disadvantages inherent in the known types of support belts now present in the prior art, the present invention provides a new inflatable support device construction wherein the same can be utilized for supporting the lower back of a user especially when the user is sitting.

The general purpose of the present invention, which will be described subsequently in greater detail, is to provide a new inflatable support device apparatus and method which has many of the advantages of the support belts mentioned heretofore and many novel features that result in a new inflatable support device which is not anticipated, rendered obvious, suggested, or even implied by any of the prior art support belts, either alone or in any combination thereof.

To attain this, the present invention generally comprises an elongate flexible belt adapted for wrapping around the waist area of a wearer. An inflatable waist bladder is coupled to the belt such that the waist bladder is wrapped around the waist area of the wearer when the belt is wrapped around the waist area of the wearer. An elongate lower support bar downwardly depends from the belt. The lower support bar is designed for positioning adjacent the spine region of the lower back area of the wearer to provide support to the lower back area of the wearer. The lower support bar has opposite top and bottom ends, and a pair of side edges extending between the top and bottom ends of the lower support bar. The top end of the lower support bar is attached to the belt. A flexible flap is extended from the bottom end of the lower support bar. The flexible flap is designed for sitting on by the wearer. The lower support bar has a pair of elongate inflatable back bladders. One of the back bladders is coupled to one of the side edges of the lower support bar. The other back bladder is coupled to the other side edge of the lower support bar.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new inflatable support device apparatus and method which has many of the advantages of the support belts mentioned heretofore and many novel features that result in a new inflatable support device which is not anticipated, rendered obvious, suggested, or even implied by any of the prior art support belts, either alone or in any combination thereof.

It is another object of the present invention to provide a new inflatable support device which may be easily and efficiently manufactured and marketed.

It is a further object of the present invention to provide a new inflatable support device which is of a durable and reliable construction.

An even further object of the present invention is to provide a new inflatable support device which is susceptible of a low cost of manufacture with regard to both materials and labor, and which accordingly is then susceptible of low prices of sale to the consuming public, thereby making such inflatable support device economically available to the buying public.

Still yet another object of the present invention is to provide a new inflatable support device which provides in the apparatuses and methods of the prior art some of the advantages thereof, while simultaneously overcoming some of the disadvantages normally associated therewith.

Still another object of the present invention is to provide a new inflatable support device for supporting the lower back of a user especially when the user is sitting.

Yet another object of the present invention is to provide a new inflatable support device which includes an elongate flexible belt adapted for wrapping around the waist area of a wearer. An inflatable waist bladder is coupled to the belt such that the waist bladder is wrapped around the waist area of the wearer when the belt is wrapped around the waist area of the wearer. An elongate lower support bar downwardly depends from the belt. The lower support bar is designed for positioning adjacent the spine region of the lower back area of the wearer to provide support to the lower back area of the wearer. The lower support bar has opposite top and bottom ends, and a pair of side edges extending between the top and bottom ends of the lower support bar. The top end of the lower support bar is attached to the belt. A flexible flap is extended from the bottom end of the lower support bar. The flexible flap is designed for sitting on by the wearer. The lower support bar has a pair of elongate inflatable back bladders. One of the back bladders is coupled to one of the side edges of the lower support bar. The other back bladder is coupled to the other side edge of the lower support bar.

Still yet another object of the present invention is to provide a new inflatable support device that may be worn while riding a bicycle or a motorcycle to provide additional back support to help reduce fatigue from sitting on the bicycle or motorcycle.

Even still another object of the present invention is to provide a new inflatable support device that is inflatable to comfortably fit and support the wearer.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic front perspective view of the present invention.

FIG. 4 is a schematic cross sectional view of an inflation mechanism of the present invention taken from line 4—4 of FIG. 3.

DESCRIPTION OF THE PREFERRED EMBODIMENT

Figure 1:
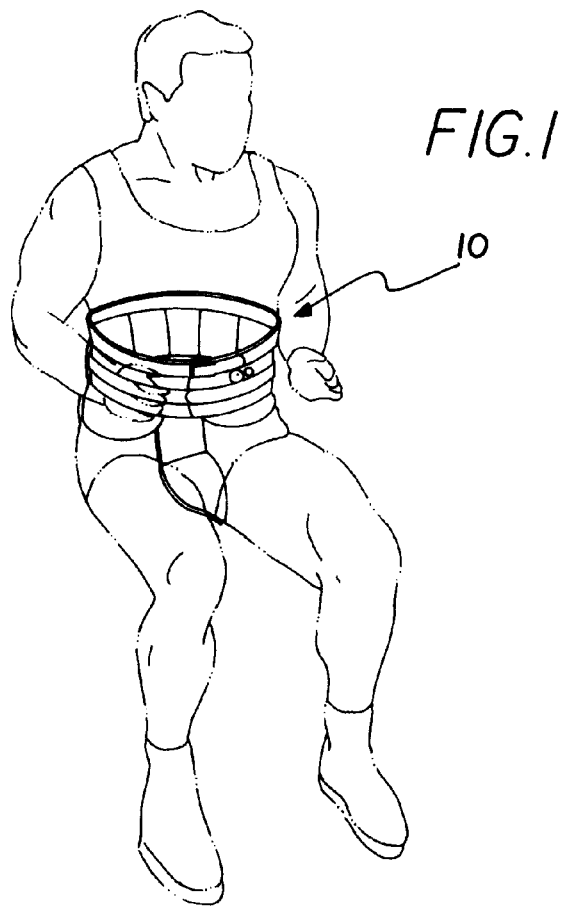
FIG. 1 is a schematic perspective view of a new inflatable support device in use according to the present invention.

With reference now to the drawings, and in particular to FIGS. 1 through 6 thereof, a new inflatable support device embodying the principles and concepts of the present invention and generally designated by the reference numeral 10 will be described.

As best illustrated in FIGS. 1 through 6, the inflatable support device 10 generally comprises an elongate flexible belt 11 adapted for wrapping around the waist area of a wearer. An inflatable waist bladder 14 is coupled to the belt 11 such that the waist bladder 14 is wrapped around the waist area of the wearer when the belt 11 is wrapped around the waist area of the wearer. An elongate lower support bar 28 downwardly depends from the belt 11. The lower support bar 28 is designed for positioning adjacent the spine region of the lower back area of the wearer to provide support to the lower back area of the wearer. The lower support bar 28 has opposite top and bottom ends 29,30, and a pair of side edges 31,32 extending between the top and bottom ends 29,30 of the lower support bar 28. The top end 29 of the lower support bar 28 is attached to the belt 11. A flexible flap 34 is extended from the bottom end 30 of the lower support bar 28. The flexible flap 34 is designed for sitting on by the wearer. The lower support bar 28 has a pair of elongate inflatable back bladders 35,36. One of the back bladders 35 is coupled to one of the side edges 31 of the lower support bar 28. The other back bladder 36 is coupled to the other side edge 32 of the lower support bar 28.

In closer detail, the elongate flexible belt 11 is adapted for wrapping around the waist area of a wearer. The belt 11 has a pair of opposite ends and inner and outer sides. The inner side of the belt 11 faces towards the wearer when the belt 11 is wrapped around the waist area of the wearer. The ends of the belt 11 are attachable together when the belt 11 is wrapped around the waist area of the wearer. As illustrated in FIG. 3, a hook and loop fastener 13 preferably detachably attaches the ends of the belt 11 together. Optionally, a buckle may detachably attach the ends of the belt 11 together instead of the hook and loop fastener.

The inflatable waist bladder 14 is coupled to the inner surface of the belt 11 such that the waist bladder 14 is wrapped around the waist area of the wearer when the belt 11 is wrapped around the waist area of the wearer. The waist bladder 14 has inner and outer faces 15,16. In use, the inner face 15 of the inflatable waist bladder 14 faces towards the wearer when the waist bladder 14 is wrapped around the waist area of the wearer. The outer face 16 of the waist bladder 14 is coupled to the inner surface of the belt 11. The waist bladder 14 has a pair of opposite ends 17,18 and a pair of sides 19,20 extending between the ends 17,18 of the waist bladder 14. Each end 17,18 of the waist bladder 14 is positioned adjacent an associated end of the belt 11. Preferably, the belt 11 is positioned along a midline between the sides 19,20 of the waist belt 11. Ideally, the waist bladder 14 has a cloth fabric outer layer for providing additional comfort to the wearer. The waist bladder 14 is inflatable and deflatable to provide comfortable and snug support around the waist area of the wearer (including the associated back area of the wearer). The waist bladder 14 preferably comprises a number of inflatable cells for helping insure a proper shape to the inflated waist bladder 14.

With reference to FIG. 4, the waist bladder 14 has an inflation mechanism 22 for inflating the waist bladder 14. The inflation mechanism 22 of the waist bladder 14 preferably comprises a hand pump 23 for pumping air into the waist bladder 14 and a one-way air valve 24 for permitting the passage of air pumped into the waist bladder 14 by the hand pump 23. The hand pump 23 of the inflation mechanism 22 is provided on the outer face 16 of the waist bladder 14 between the belt 11 and the lower side of the waist bladder 14 and adjacent one of the ends of the waist bladder 14.

Figure 5:
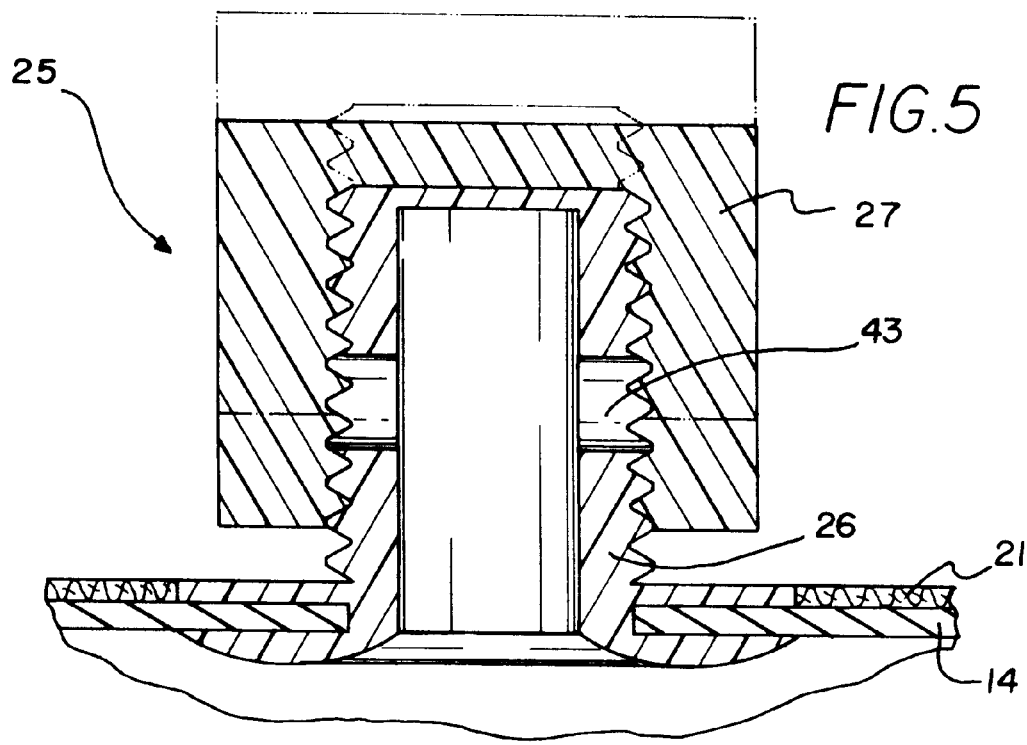
FIG. 5 is a schematic cross sectional view of a deflation mechanism of the present invention taken from line 5—5 of FIG. 3.

With reference to FIG. 5, the waist bladder 14 also has a deflation mechanism 25 for selectively deflating the waist bladder 14. The deflation mechanism 25 of the waist bladder 14 is provided on the outer face 16 of the waist bladder 14 adjacent the inflation mechanism 22. The deflation mechanism 25 of the waist bladder 14 has a threaded stem 26 providing an opening 43 into the waist bladder 14 and a threaded cap 27 threaded on to the threaded stem 26 to close the opening 43 of the threaded stem 26. In use, un-tightening of the threaded cap 27 on the threaded stem 26 permits the release of air from in the waist bladder 14 through the opening 43 of the threaded stem 26 to deflate the waist bladder.

Figure 2:
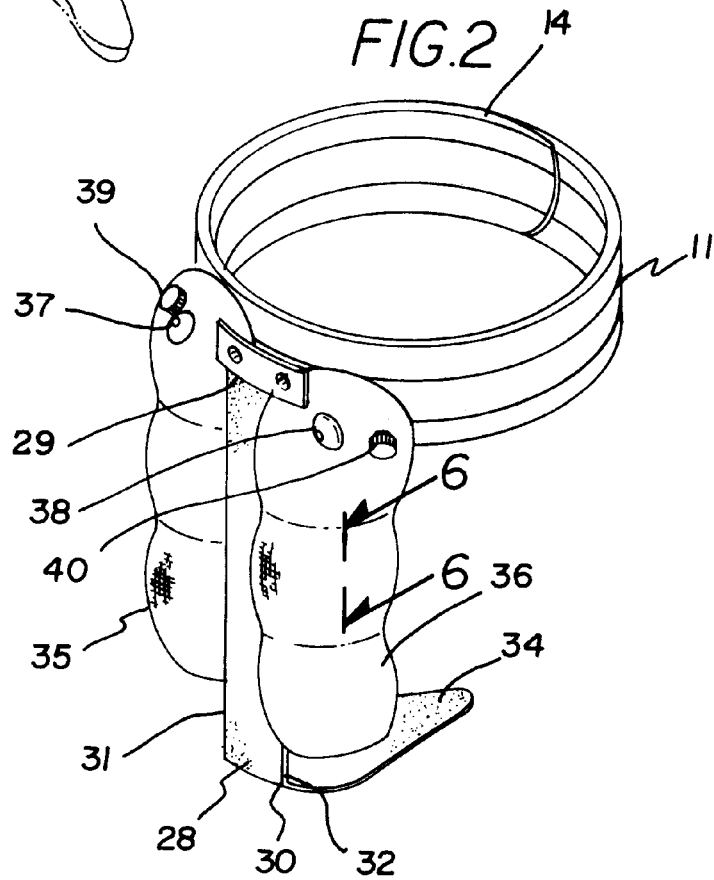
FIG. 2 is a schematic perspective view of the back of the present invention.

The generally rigid elongate lower support bar 28 downwardly depends from the belt 11. The lower support bar 28 is designed for positioning adjacent the spine region of the lower back area of the wearer to provide support to the lower back area of the wearer. As best illustrated in FIG. 2, the lower support bar 28 is generally rectangular and has front and back surfaces, opposite top and bottom ends 29,30, and a pair of generally straight side edges 31,32 extending between the top and bottom ends 29,30 of the lower support bar 28. The top end 29 of the lower support bar 28 is attached to the belt 11 preferably at a midpoint between the ends of the belt 11 such that the lower support bar 28 downwardly depends from the belt 11. Preferably, a pair of fasteners 33 detachably attach the top end 29 of the lower support bar 28 to the outer side of the belt 11, Ideally, the fasteners 33 comprise snap fasteners 33. The belt 11 has a length defined between the ends of the belt 11 and the lower support bar 28 has a longitudinal axis extending between the top and bottom ends 29,30 of the lower support bar 28. The longitudinal axis of the lower support bar 28 preferably downwardly extends generally perpendicular to the length of the belt 11.

Figure 6:
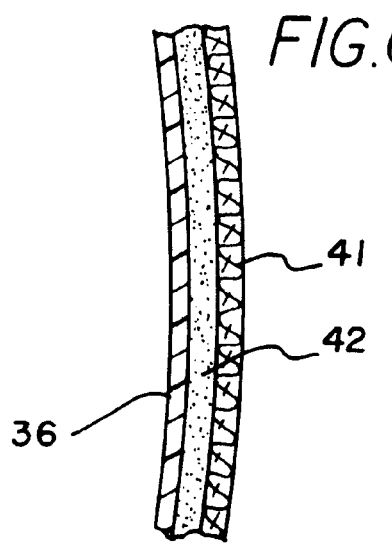
FIG. 6 is a schematic cross sectional view of a broken away portion of a back bladder of the present invention taken from line 6—6 of FIG. 2.

The lower support bar 28 has a pair of elongate inflatable back bladders 35,36. One of the back bladders 35 is coupled to one of the side edges 31 of the lower support bar 28 while the other back bladders 36 is coupled to the other side edge 32 of the lower support bar 28. Each of the back bladders 35,36 has a length extending between the top and bottom ends 29,30 of the lower support rod. Each of the back bladders 35,36 preferably comprises a number of inflatable cells for helping insure a proper shape to an inflated back bladder. As illustrated in FIG. 6, each back bladder preferably has a outer cloth fabric layer 41 and middle foamed material layer 42 for providing added comfort to the wearer.

Each of the back bladders 35,36 has an inflation mechanism 37,38 for inflating the back bladder. The inflation mechanism 37,38 of each of the back bladders 35,36 preferably comprises a similar mechanism as the inflation mechanism 22 of the waist bladder 14. Each of the back bladders 35,36 has a deflation mechanism 39,40 for selectively deflating the back bladders. The deflation mechanism 39,40 of each of the back bladders 35,36 preferably comprises a similar deflation mechanism 25 of the waist bladder.

The flexible flap 34 is extended from the bottom end 30 of the lower support bar 28. The flexible flap 34 is preferably generally triangular and is designed for sitting on by the wearer. In one preferred embodiment, the flexible flap 34 comprises a flexible leather. Ideally, the flexible flap comprises an inflatable bladder like the back bladders that is connected by a conduit such a flexible tube directly to the inflation mechanism 37 so that the flexible flap 34 may be inflated by the inflation mechanism into an inflated triangular form for providing an inflated cushion or pad for the wearer sitting on it.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A support device, comprising:

an elongate flexible belt adapted for wrapping around the waist area of a wearer;

an inflatable waist bladder being coupled to said belt such that said waist bladder is wrapped around the waist area of the wearer when said belt is wrapped around the waist area of the wearer;

an elongate lower support bar downwardly depending from said belt, said lower support bar being adapted for positioning adjacent the spine region of the lower back area of the wearer to provide support to the lower back area of the wearer;

said lower support bar having opposite top and bottom ends, and a pair of side edges extending between said top and bottom ends of said lower support bar;

said top end of said lower support bar being attached to said belt;

a flexible flap being extended from said bottom end of said lower support bar, said flexible flap being adapted for sitting on by the wearer; and said lower support bar having a pair of elongate inflatable back bladders, one of said back bladders being coupled to one of said side edges of said lower support bar, another of said back bladders being coupled to another of said side edges of said lower support bar.

2. The support device of claim 1, wherein said belt has a pair of opposite ends, said ends of said belt being attachable together when said belt is wrapped around the waist area of the wearer.

3. The support device of claim 2, wherein a buckle detachably attaches said ends of said belt together.

4. The support device of claim 2, wherein a hook and loop fastener detachably attaches said ends of said belt together.

5. The support device of claim 1, wherein said waist bladder is inflatable and deflatable, said waist bladder having an inflation mechanism for inflating said waist bladder, said waist bladder having a deflation mechanism for selectively deflating said waist bladder.

6. The support device of claim 5, wherein said inflation mechanism of said waist bladder -has a hand pump for pumping air into said waist bladder and a one-way air valve for permitting the passage of air pumped into said waist bladder by said hand pump.

7. The support device of claim 1, wherein a pair of fasteners detachably attach said top end of said lower support bar to said outer side of said belt.

8. The support device of claim 1, wherein said belt has a length defined between said ends of said belt, wherein said lower support bar has a longitudinal axis extending between said top and bottom ends of said lower support bar, and wherein said longitudinal axis of said lower support bar is extended generally perpendicular to said length of said belt.

9. The support device of claim 1, wherein each of said back bladders has an inflation mechanism for inflating said back bladder, wherein each of said back bladders has a deflation mechanism for selectively deflating said back bladder.

10. A support device, comprising:

an elongate flexible belt adapted for wrapping around the waist area of a wearer, said belt having a pair of opposite ends and inner and outer sides, said inner side of said belt facing towards the wearer when said belt is wrapped around the waist area of the wearer, said ends of said belt being attachable together when said belt is wrapped around the waist area of the wearer;

wherein a buckle detachably attaches said ends of said belt together;

an inflatable waist bladder being coupled to said inner surface of said belt such that said waist bladder is wrapped around the waist area of the wearer when said belt is wrapped around the waist area of the wearer;

said waist bladder having inner and outer faces, said inner face of said inflatable waist bladder facing towards the wearer when said waist bladder is wrapped around the waist area of the wearer, said outer face of said waist bladder being coupled to said inner surface of said belt;

said waist bladder having a pair of opposite ends and a pair of sides extending between said ends of said waist bladder, each end of said waist bladder being positioned adjacent an associated end of said belt, said belt being positioned along a midline between said sides of said waist belt;

wherein said waist bladder has a cloth fabric outer layer for providing additional comfort to the wearer;

said waist bladder being inflatable and deflatable;

said waist bladder having an inflation mechanism for inflating said waist bladder, said inflation mechanism of said waist bladder having a hand pump for pumping air into said waist bladder and a one-way air valve for permitting the passage of air pumped into said waist bladder by said hand pump;

said hand pump of said inflation mechanism being provided on said outer face of said waist bladder;

said waist bladder having a deflation mechanism for selectively deflating said waist bladder, said deflation mechanism of said waist bladder being provided on said outer face of said waist bladder;

an elongate lower support bar downwardly depending from said belt, said lower support bar being adapted for positioning adjacent the spine region of the lower back area of the wearer to provide support to the lower back area of the wearer;

said lower support bar being generally rectangular and having front and back surfaces, opposite top and bottom ends, and a pair of generally straight side edges extending between said top and bottom ends of said lower support bar;

said top end of said lower support bar being attached to said belt at a midpoint between said ends of said belt such that said lower support bar downwardly depends from said belt;

wherein a pair of fasteners detachably attach said top end of said lower support bar to said outer side of said belt, wherein said fasteners comprise snap fasteners;

said belt having a length defined between said ends of said belt, said lower support bar having a longitudinal axis extending between said top and bottom ends of said lower support bar, said longitudinal axis of said lower support bar being extended generally perpendicular to said length of said belt;

a flexible flap being extended from said bottom end of said lower support bar, said flexible flap being generally triangular and being adapted for sitting on by the wearer, wherein said flexible flap comprises a flexible leather;

said lower support bar having a pair of elongate inflatable back bladders, one of said back bladders being coupled to one of said side edges of said lower support bar, another of said back bladders being coupled to another of said side edges of said lower support bar, each of said back bladders having a length extending between said top and bottom ends of said lower support rod;

each of said back bladders having an inflation mechanism for inflating said back bladder; and each of said back bladders having a deflation mechanism for selectively deflating said back bladder.

* * * * *